(12) United States Patent
Stromereder et al.

(10) Patent No.: US 8,840,766 B2
(45) Date of Patent: Sep. 23, 2014

(54) GAS-MONITORING ASSEMBLY COMPRISING ONE OR MORE GAS SENSORS AND ONE OR MORE GETTERS, AND METHOD OF USING SAME

(75) Inventors: Stefan Stromereder, Munich (DE); Peter Koller, Schaeftlarn (DE)

(73) Assignee: Honeywell International, Inc., Northford, CT (US)

( * ) Notice: Subject to any disclaimer, the term of this patent is extended or adjusted under 35 U.S.C. 154(b) by 0 days.

(21) Appl. No.: 13/454,616

(22) Filed: Apr. 24, 2012

(65) Prior Publication Data

US 2012/0205244 A1    Aug. 16, 2012

Related U.S. Application Data

(62) Division of application No. 11/571,500, filed as application No. PCT/EP2005/006993 on Jun. 29, 2006, now Pat. No. 8,163,149.

(51) Int. Cl.
  *G01N 27/403*   (2006.01)
  *G01J 1/50*     (2006.01)

(52) U.S. Cl.
  USPC ......... 204/431; 205/775; 73/23.31; 73/23.32; 422/86

(58) Field of Classification Search
  USPC ............... 204/400, 401, 431, 432, 421–430; 205/775; 422/86, 87; 73/23.2, 23.21, 73/23.32, 23.31
  See application file for complete search history.

(56) References Cited

U.S. PATENT DOCUMENTS

| | | |
|---|---|---|
| 4,115,067 A | 9/1978 | Lyshkow |
| 4,181,699 A | 1/1980 | Kitzinger |
| 4,326,200 A | 4/1982 | Bushman |
| 4,532,120 A | 7/1985 | Smith et al. |
| 5,112,456 A | 5/1992 | Worrell et al. |
| 6,248,224 B1 | 6/2001 | Kitzelmann |
| 6,251,244 B1 | 6/2001 | Kiesele et al. |
| 6,423,209 B1 | 7/2002 | Weber et al. |
| 6,855,557 B2 | 2/2005 | Kishkovich et al. |
| 7,140,229 B2 | 11/2006 | Stromereder et al. |
| 2002/0094298 A1 | 7/2002 | Monagan |
| 2004/0083792 A1 | 5/2004 | Nikolskaya |
| 2004/0129565 A1 | 7/2004 | Prohaska et al. |

FOREIGN PATENT DOCUMENTS

| | | |
|---|---|---|
| EP | 0280540 A2 | 8/1988 |
| FR | 2541461 A1 | 8/1984 |
| GB | 2135780 A | 9/1984 |

OTHER PUBLICATIONS

City Technology, "Toxic Gas CiTicels", "City Technology Manual", published on or before Jul. 20, 1999, pp. 2-39.
Krupay, B., et al., "The heterogeneous catalytic reaction between carbon monoxide and nitrous oxide over manganous oxide and cobalto-cobaltic oxide", "Canadian Journal of Chemistry", 1978, pp. 10-16, vol. 56, No. 1.

*Primary Examiner* — Jennifer Dieterle
(74) *Attorney, Agent, or Firm* — Hultquist, PLLC; Steven J. Hultquist

(57) ABSTRACT

The present invention relates to a gas-monitoring assembly (100) and method for selectively determining the presence of a target gas in a gaseous environment that potentially comprises one or more interfering gases. Such gas-monitoring assembly and method specifically employ one or more gas sensors (S1) one or more getters (G1) arranged and constructed to reduce cross-interference caused by potential presence of the interfering gases in such gaseous environment to be monitored. The gas-monitoring assembly and method of the present invention are capable of monitoring a gaseous environment with respect to potential presence of multiple target gases that may interfere with one another.

2 Claims, 16 Drawing Sheets

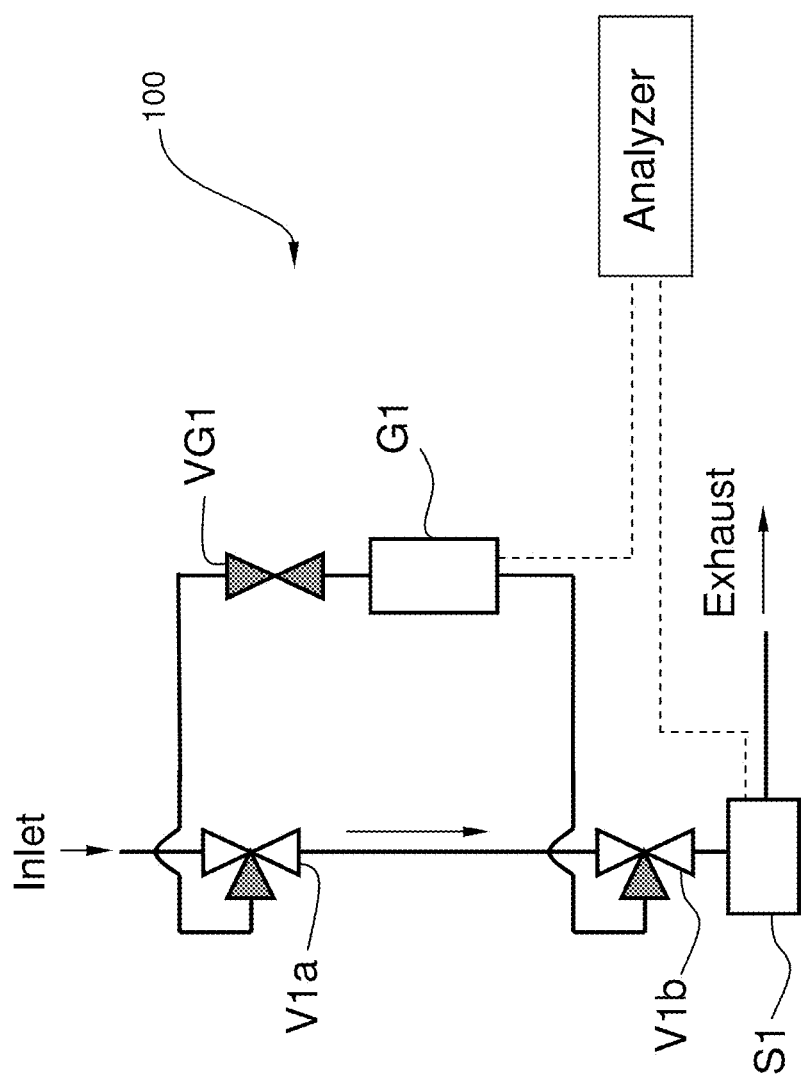

GAS-MONITORING ASSEMBLY COMPRISING ONE OR MORE GAS SENSORS AND ONE OR MORE GETTERS, AND METHOD OF USING SAME

CROSS REFERENCE TO RELATED APPLICATIONS

This application is a divisional of application Ser. No. 11/571,500, filed Dec. 29, 2006, now U.S. Pat. No. 8,163,149, which is the National Stage of International Application No. PCT/EP2005/006993, Jun. 29, 2005, which claims the benefit of U.S. patent application Ser. No. 10/880,248 filed Jun. 29, 2004, now U.S. Pat. No. 7,140,229. The disclosures of said International Patent Application and said U.S. patents are hereby incorporated herein by reference, in their respective entireties.

FIELD OF THE INVENTION

The present invention relates to gas-monitoring assemblies and methods for selectively determining presence of one or more target gases in a gaseous environment, while reducing cross-interference caused by presence of one or more interfering gases in such gaseous environment.

DESCRIPTION OF THE RELATED ART

In order to protect workers against potential exposure to toxic and hazardous gases, toxic/hazardous gas monitoring (TGM) devices are commonly installed in workplace and other premises for monitoring the concentration of such toxic and hazardous gases threat.

Conventional TGM devices employ molecular emission spectrometers for hydrogen-based gas detection. However, the introduction of hydrogen gas gives rise to additional safety concerns and requires implementation of additional safety measures to reduce risks associated with hydrogen gas.

New TGM systems employing electrochemical gas sensors can be advantageously used for monitoring toxic and hazardous gases, in place of the conventional hydrogen-based TGM devices. The use of electrochemical gas sensors eliminates the risks associated with hydrogen gas and therefore results in increased customer acceptance.

In electrochemical gas-sensing systems, a target gas contacts a measuring electrode of the electrochemical sensor, which responsively generates an electrical current that is proportional to the concentration of such target gas. For further details regarding electrochemical gas sensors, see U.S. Pat. No. 6,248,224 issued on Jun. 19, 2001 for "TOXIC SENSOR AND METHOD OF MANUFACTURE" and U.S. Pat. No. 6,423,209 issued on Jul. 23, 2002 for "ACID GAS MEASURING SENSORS AND METHOD OF USING SAME."

However, gases that belong to the same chemical family often show similar or comparable reactions in the same electrochemical cell and cause cross-interference in the electrochemical measurement results. Currently available electrochemical gas sensors not only respond to the presence of a target gas, but also to presence of other gases of the same chemical family.

For example, an $AsH_3$ sensor responds not only responds to $AsH_3$ gas, but also to other hydride gases such as $B_2H_6$, $SiH_4$, and $PH_3$. The measuring electrode of such $AsH_3$ sensor reacts with the $AsH_3$ gas as follows:

$$AsH_3 + 3H_2O \rightarrow H_3AsO_3 + 6H^+ + 6e^-,$$

while it also reacts with $SiH_4$, an interfering hydride, as follows:

$$SiH_4 + 3H_2O \rightarrow H_2SiO_3 + 8H^+ + 8e^-$$

Therefore, the interfering gases will trigger the electrochemical gas sensor to generate signals indicating the presence of the target gas, even when the target gas is actually absent (i.e., false alarm).

It is therefore one object of the present invention to provide an apparatus and method for reducing such false alarm and increasing the selectivity of electrochemical gas sensors.

It is another object of the present invention to provide an apparatus and method for increasing selectivity of other types of gas sensors whose measurement results are similarly affected by presence of interfering gases and are prone to false alarm.

Other objects and advantages will be more fully apparent from the ensuring disclosure and appended claims.

SUMMARY OF THE INVENTION

The present invention in one aspect relates to a gas-monitoring assembly that comprises:

(a) one or more gas sensors for monitoring concentration of a target gas in a gaseous environment, wherein the target gas concentration detected by the gas sensors is susceptible to influence by presence of one or more interfering gas species in such gaseous environment;

(b) one or more getters coupled with such gas sensors and being arranged and constructed to adsorb the target gas and/or the interfering gas species upon detection of the target gas concentration above a predetermined level in such gaseous environment; and (c) an analyzer coupled with the one or more gas sensors and the one or more getters for selectively determining the presence of the target gas in such gaseous environment, based on detected changes in the target gas concentration caused by interaction of the target gas with the one or more getters in relation to target gas concentration absent such interaction.

The term "getter" as used herein refers to a material or an article that selectively adsorbs one or more gases and therefore is capable of selectively removing such gases from a gaseous mixture.

The terms "interfering gas species" and "interfering gas" are used interchangeably herein to refer to a gas that is different from the target gas to be detected but is capable of inducing responses in a target gas sensor in a manner that is identical or similar to the target gas.

Preferably, the target gas is a hydride gas, while the interfering gas species are one or more hydride gases that are different from the target gas.

More preferably, the target gas is a hydride gas selected from the group consisting of $AsH_3$, $B_2H_6$, and $SiH_4$, while the interfering gas species are selected from the same group of hydride gases but are different from the target gas.

The presence of the target gas in the gaseous environment can be directly determined by using a getter that selectively adsorbs the target gas (i.e., a target-specific getter). Specifically, when the gas sensor detects a high concentration (i.e., above a predetermined level) of the target gas in the gaseous environment, the target-specific getter is arranged and constructed for adsorbing the target gas. Within a predetermined time interval after interaction of such target-specific getter with the target gas, if the detected target gas concentration is found to reduce to below a predetermined threshold, the analyzer affirms the presence of the target gas in the gaseous environment; on the other hand, if the detected target gas concentration is found to remain equal to or above such predetermined threshold after expiration of such predetermined time interval, the analyzer does not affirm the presence of the target gas in the gaseous environment.

Alternatively, the presence of the target gas in the gaseous environment can be indirectly inferred by using a set of getters that include a first getter that adsorbs the target gas as well as the interfering gases and additional getters that each selectively adsorbs one of the interfering gases (i.e., interference-specific getter). Such first getter and the additional getters are sequentially employed to interact with the gaseous environment when the gas sensor detects a high concentration (i.e., above a predetermined level) of the target gas in the gaseous environment. Such first getter is associated with a first predetermined time interval and a predetermined concentration threshold, while each of such additional getters is associated with an additional predetermined time interval and an additional predetermined concentration threshold. The analyzer affirms the presence of the target gas in the gaseous environment, only if (1) the detected gas concentration is found to reduce below the first predetermined concentration threshold within the first predetermined time interval after employment of the first getter, and (2) the detected gas concentration is found to remain equal to or above the respective additional predetermined concentration threshold within the respective additional predetermined time interval after employment of each interference-specific getter. In all other situations, the analyzer does not affirm the presence of the target gas in the gaseous environment.

The gas-monitoring assembly described hereinabove preferably comprises an alarm device coupled with such analyzer, for generating an alarm signal whenever the presence of the target gas in the gaseous environment is affirmed by the analyzer.

The gas sensor of the present invention is preferably, but not necessarily, an electrochemical gas sensor that comprises an electrolyte in contact with a measuring electrode, a reference electrode, and a counter electrode.

In a specific embodiment of the present invention, the gas-monitoring assembly comprises an electrochemical gas sensor for monitoring concentration of $AsH_3$ gas in a gaseous environment, and a getter for selectively adsorbing $AsH_3$ gas.

In another specific embodiment of the present invention, the gas-monitoring assembly comprises an electrochemical gas sensor for monitoring concentration of $B_2H_6$ gas in a gaseous environment, and a getter for selectively adsorbing $B_2H_6$ gas.

In yet another specific embodiment of the present invention, the gas-monitoring assembly comprises (1) an electrochemical gas sensor for monitoring concentration of $SiH_4$ gas in a gaseous environment, (2) a first getter for adsorbing $AsH_3$, $B_2H_6$, and $SiH_4$ gases, (3) a second getter for selectively adsorbing $B_2H_6$ gas, and (4) a third getter for selectively adsorbing $AsH_3$ gas.

The present invention in another aspect relates to a gas-monitoring assembly that comprises at least one gas sensor, at least one getter, and a control element, wherein the gas sensor monitors concentration of a target gas in a gaseous environment, wherein the getter comprises material that selectively adsorbs the target gas, and wherein the control element is coupled with the gas sensor and the getter for enabling interaction of the gaseous environment with the getter when the target gas concentration detected by the gas sensor exceeds a predetermined level.

The present invention in a further aspect relates to a gas-monitoring assembly that comprises at least one gas sensor and a gas analysis circuitry, wherein such gas sensor monitors concentration of a target gas in a gaseous environment, wherein the gas analysis circuitry comprises one or more getters, and wherein such gas analysis circuitry is activated upon detection of target gas concentration above a predetermined level, for selectively determining presence of the target gas in the gaseous environment while reducing potential cross-interference caused by presence of one or more interfering gas species in the gaseous environment.

The present invention in a still further aspect relates to a gas-monitoring assembly that comprises:

(a) multiple gas sensors, each of which monitors concentration of one of multiple target gases in a gaseous environment, wherein the concentration of each target gas detected by the respective gas sensor is susceptible to influence by presence of one or more other target gases in such gaseous environment;

(b) multiple getters coupled with such multiple gas sensors in such manner that one or more of such multiple getters are sequentially employed for adsorbing one or more of the target gases upon detection of concentration of at least one target gas above a predetermined level; and (c) an analyzer coupled with such multiple gas sensors and such multiple getters for selectively determining the presence of at least one target gas in the gaseous environment, based on detected changes in the concentration of such at least one target gas caused by interaction of such at least one target gas with such one or more getters in relation to target gas concentration absent such interaction.

In a specific embodiment of the present invention, the above-described gas-monitoring assembly comprises: (1) a first electrochemical gas sensor for monitoring concentration of $AsH_3$ gas; (2) a second electrochemical gas sensor for monitoring concentration of $B_2H_6$ gas; (3) a third electrochemical gas sensor for monitoring concentration of $SiH_4$ gas, (4) a first getter the selectively adsorbs $AsH_3$ gas, (5) a second getter that selectively adsorbs $B_2H_6$ gas; and (6) a third getter that adsorbs $AsH_3$, $B_2H_6$, and $SiH_4$ gases.

For $AsH_3$ analysis, the first getter is employed for adsorbing the $AsH_3$ gas when concentration of the $AsH_3$ gas in a gaseous environment is found to exceed a predetermined level. Within a predetermined time interval (which is specific for $AsH_3$ analysis) after employment of the $AsH_3$ getter, if the detected $AsH_3$ concentration is found to reduce to below a predetermined threshold (which is specific for $AsH_3$ analysis), the analyzer affirms presence of the $AsH_3$ gas in such gaseous environment. On the other hand, if the detected $AsH_3$ within such time interval is found to remain equal to or above such predetermined threshold, the analytic element does not affirm the presence of the $AsH_3$ gas.

For $B_2H_6$ analysis, the second getter is employed for adsorbing the $B_2H_6$ gas when concentration of the $B_2H_6$ gas in the gaseous environment is found to exceed a predetermined level. Within a predetermined time interval (which is specific for $B_2H_6$ analysis) after employment of the $B_2H_6$ getter, if the detected $B_2H_6$ concentration is found to reduce to below a predetermined threshold (which is specific for $B_2H_6$ analysis), the analyzer affirms presence of the $B_2H_6$ gas in such gaseous environment. On the other hand, if the detected $B_2H_6$ within such time interval is found to remain equal to or above such predetermined threshold, the analytic element does not affirm the presence of the $B_2H_6$ gas.

For $SiH_4$ analysis, the first, second, and third getters are sequentially employed, either in a predetermined order or in a random order, for adsorbing the respective gases when concentration of the $SiH_4$ gas in the gaseous environment is found to exceed a predetermined level. The analyzer affirms the presence of the $SiH_4$ gas, only if (1) within a predetermined time interval (which is specific for $SiH_4$ analysis) after employment of the third getter, if the detected gas concentration is found to reduce to below a predetermined threshold (which is specific for $SiH_4$ analysis), and (2) within the respective predetermined time interval specific for $AsH_3$ or $B_2H_6$ analysis after employment of the respective $AsH_3$— or $B_2H_6$-specific getter, the detected gas concentration is found to remain equal to or above the predetermined threshold specific for $AsH_3$ or $B_2H_6$ analysis.

Another aspect of the present invention relates to a method for selectively determining presence of a target gas in a gaseous environment, comprising the steps of:

(a) monitoring concentration of the target gas in such gaseous environment by using one or more gas sensors, wherein the target gas concentration detected by the gas sensors is susceptible to influence by presence of one or more interfering gas species in such gaseous environment;

(b) coupling such gas sensors with one or more getters and an analyzer;

(c) when the target gas concentration in the gaseous environment is detected to exceed a predetermined level, employing such one or more getters to adsorb the target gas and/or one or more interfering gas species;

(d) selectively determining the presence of the target gas in such gaseous environment by using the analyzer, based on detected changes in the target gas concentration caused by interaction of the target gas with such one or more getters in relation to target gas concentration absent such interaction.

A further aspect of the present invention relates to a method for selectively determining presence of a target gas in a gaseous environment, comprising at least the steps of:

(a) monitoring concentration of the target gas in such gaseous environment by using at least one gas sensor;

(b) coupling such at least one gas sensor with at least one getter and a control element; and (c) when the target gas concentration detected by the gas sensor exceeds a predetermined level, employing the getter through the control element to selectively adsorb the target gas.

A still further aspect of the present invention relates to a method for selectively determining presence of a target gas in a gaseous environment, comprising the steps of:

(a) monitoring concentration of the target gas in such gaseous environment by using at least one gas sensor; and (b) when the target gas concentration detected by the gas sensor exceeds a predetermined level, activating a gas analysis circuitry that comprises one or more getters for selectively determining presence of the target gas in such gaseous environment while reducing potential cross-interference caused by presence of one or more interfering gas species in such gaseous environment.

Yet another aspect of the present invention relates to a method for selectively determining presence of multiple target gases in a gaseous environment, comprising the steps of:

(a) monitoring concentrations of multiple target gases in the gaseous environment, by using multiple gas sensors that each monitor concentration of one of such multiple target gases, wherein the concentration of each target gas detected by the respective gas sensor is susceptible to influence by presence of one or more other target gases in the gaseous environment;

(b) coupling such multiple gas sensors with multiple getters and an analyzer;

(c) when concentration of at least one target gas is detected to exceed a predetermined level, sequentially employing one or more of such multiple getters so as to adsorb one or more of the multiple target gases; and (d) selectively determining the presence of such at least one target gas by using the analyzer, based on detected changes in the concentration of such at least one target gas caused by interaction of such at least one target gas with the one or more getters in relation to target gas concentration absent such interaction.

Yet a further aspect of the present invention relates to a gas monitoring assembly as described in any of the afore-mentioned aspects of the invention in combination with an optical sensor system. In one aspect, the optical sensor system is a paper-tape instrument, wherein in case of a gas exposure, color change of a chemically impregnated tape takes place. The color change can be analyzed by the optical devices provided in a preferred assembly of the invention. In a different embodiment of the invention, the color change is not analyzed by optical devices but visually inspected.

Other aspects, features and embodiments of the present invention will be more fully apparent from the ensuing disclosure and appended claims.

BRIEF DESCRIPTION OF THE DRAWINGS

FIG. 1A shows the gas flow in an illustrative gas-monitoring assembly that comprises a single gas sensor and a single getter before employment of the getter, according to one embodiment of the present invention.

DETAILED DESCRIPTION OF THE INVENTION, AND PREFERRED EMBODIMENTS THEREOF

The contents of U.S. Pat. Nos. 6,248,224 and 6,423,209 are incorporated herein by reference in their entireties for all purposes.

The present invention advantageously combines one or more gas sensors with one or more getters to form a gas-monitoring assembly with a logical operation for selectively determining the presence of a target gas of interest in a gaseous environment (e.g., a gas stream or a gas-containing enclosure), while reducing cross-interference or false alarm caused by presence of one or more interfering gases in such gaseous environment.

Figure 1B:
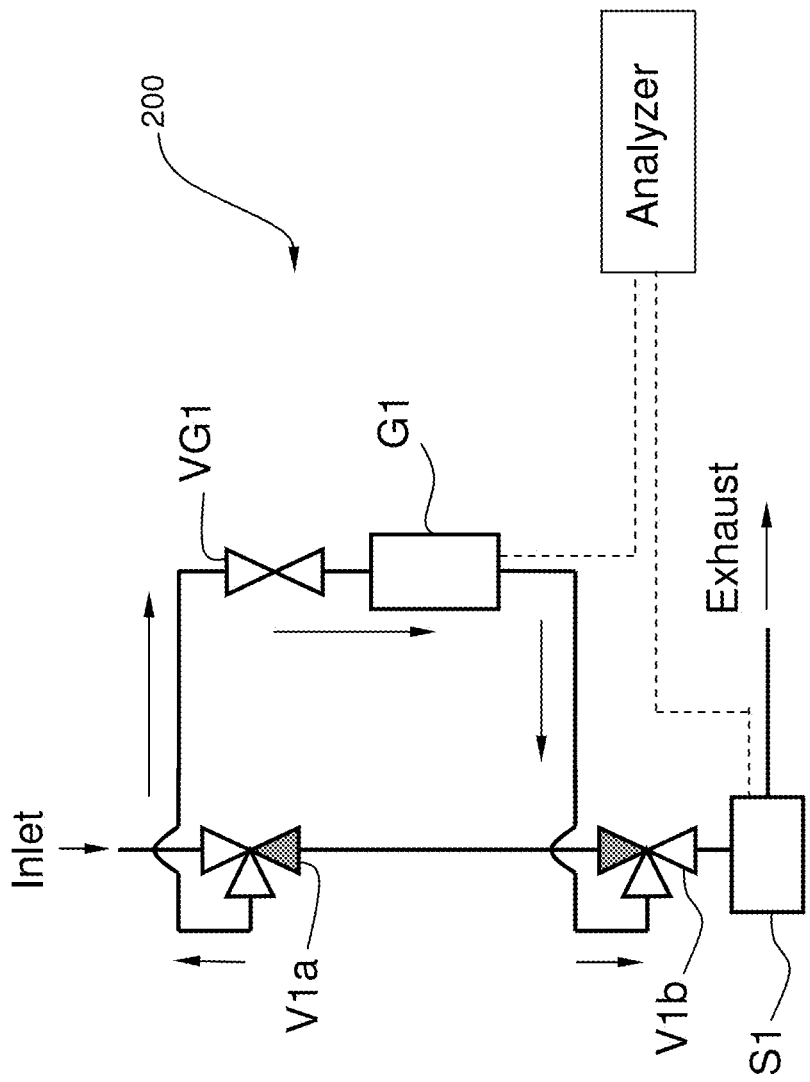
FIG. 1B shows the gas flow in the gas-monitoring assembly of FIG. 1A after employment of the getter.

FIGS. 1A and 1B illustratively show a gas-monitoring assembly 100 comprising a gas sensor S1 coupled with a getter G1. Two three-way valves V1a and V1b control gas flow through the gas sensor S1, and a getter valve VG1 controls gas flow through the getter G1. The gas sensor S1 functions to monitor the concentration of a target gas in a gaseous environment, which may also contain one or more interfering gas species that have influences upon the target gas concentration detected by the gas sensor S1 (i.e., causing cross-interference or false alarm). The getter G1, when employed, selectively adsorbs the target gas and reduces the target gas concentration.

A sample gas stream from a gaseous environment to be monitored can be first introduced into the gas-monitoring assembly 100 via an inlet, and then passed through the three-way valves V1a-V1b and the gas sensor S1 (see FIG. 1A). Therefore, the gas sensor S1 continuously monitors the concentration of a target gas in the sample gas stream passed thereby. When the target gas concentration in such sample gas stream detected by S1 exceeds a predetermined level (i.e., an alarming concentration level), a control element (not shown) opens the getter valve VG1 and switches the two three-way valves V1a-V1b to redirect the sample gas stream first through the getter G1 and then through the gas sensor S1 (see FIG. 1B).

In such manner, the getter G1 is arranged and constructed to selectively adsorb the target gas from the redirected sample gas stream, thereby reducing the target gas concentration in such sample gas stream. The change in the target gas concentration caused by interaction of the target gas with the getter G1 can be readily detected by the gas sensor S1, and an analyzer coupled with both the gas sensor S1 and the getter G1 may selectively determine the presence of the target gas in the sample gas stream, based on such detected change in the target gas concentration. Specifically, in the event when the sample gas stream contains the target gas without any interfering gas species, the getter G1 will adsorb all or most of the target gas in such sample gas stream, and result in significantly large change in the target gas concentration as sensed by S1 after employment of such getter G1. However, in the event when the sample gas stream contains one or more interfering gas species that induces response in the gas sensor S1 and causes false alarm, the detected change in the target gas concentration as sensed by S1 after employment of the getter G1 will be relatively limited, because the getter G1 selectively adsorbs the target gas but not the interfering gases. Therefore, by observing the change in the target gas concentration after employment of the getter G1, the presence of the target gas versus that of the interfering gas species in the sample gas stream can be selectively determined to reduce cross-interference or false alarm caused by such interfering gases.

As shown hereinabove, the gas-monitoring assembly of the present invention operates in two alternative modes, i.e., a first gas-monitoring mode in which only the gas sensor S1 is employed, and a second gas-analyzing mode in which both the gas sensor S1 and the getter G1 are both employed. The getter G1 forms an analytical circuitry that is activated only upon detection of high target gas concentration in the sample gas stream by the gas sensor S1. Such analytical circuitry enables further analysis of the sample gas stream, so as to reduce potential cross-interference caused by presence of one or more interference gas species in such sample gas stream.

In the gas-monitoring assembly illustrated by FIGS. 1A and 1B, the gas sensor S1 functions to detect target gas concentration in the sample gas stream, both before and after employment of the getter G1.

Figure 2A:
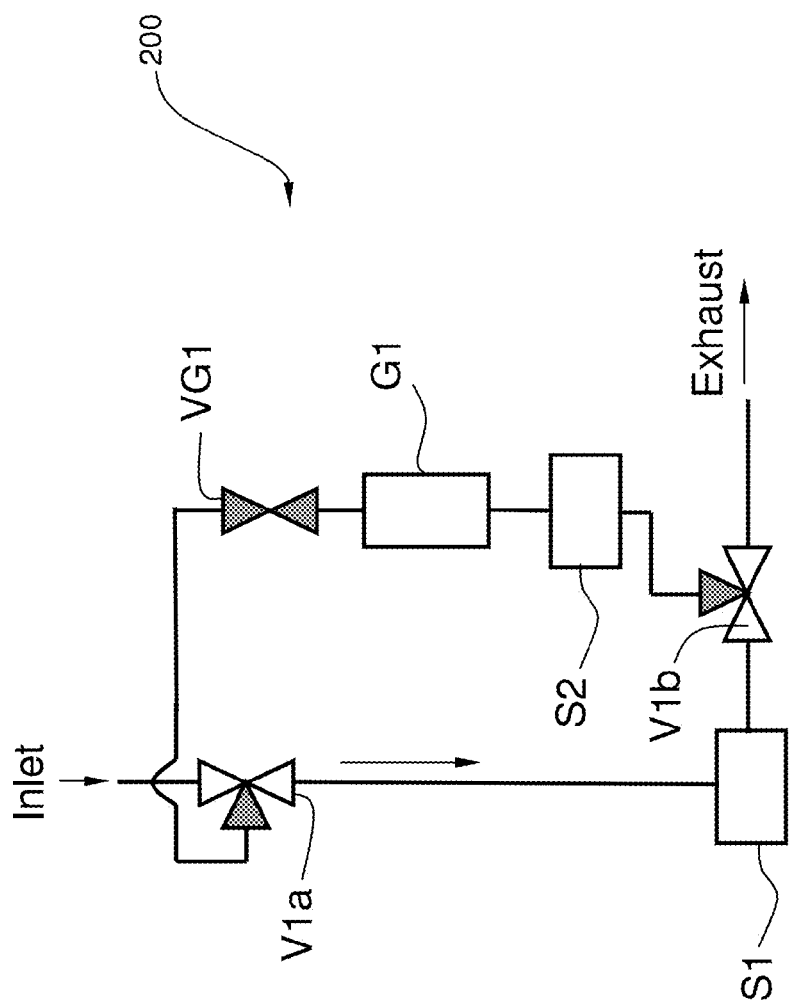
FIG. 2A shows the gas flow in an illustrative gas-monitoring assembly that comprises two gas sensors and a single getter before employment of the getter, according to one embodiment of the present invention.
Figure 2B:
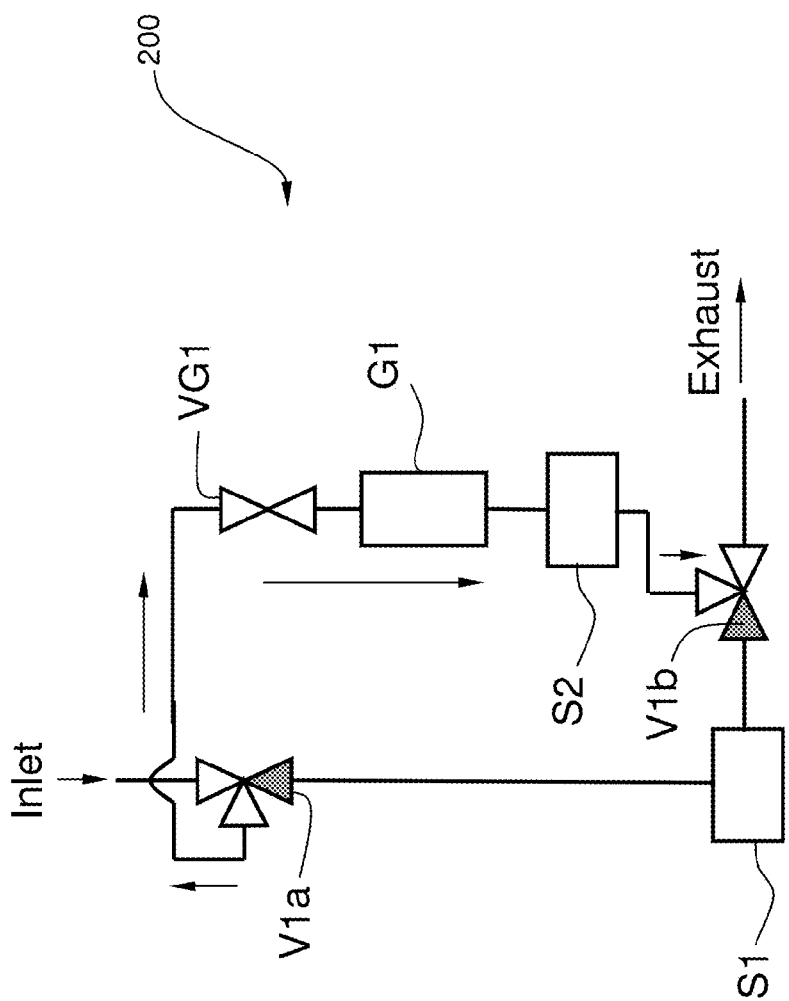
FIG. 2B shows the gas flow in the gas-monitoring assembly of FIG. 2A after employment of the getter.

Alternatively, the gas sensor S1 can be used only to detect the target gas concentration before employment of the getter G1, while an additional gas sensor S2, which is independent of S1, can be provided for monitoring the target gas concentration after employment of the getter G1, as shown in FIGS. 2A and 2B.

Specifically, FIGS. 2A and 2B illustratively show a gas-monitoring assembly 200 comprising two gas sensors S1-S2 and a getter G1.

A sample gas stream is first passed through two three-way valves V1a-V1b and the gas sensor S1 (see FIG. 2A), so that the gas sensor S1 monitors the concentration of a target gas in such sample gas stream. When the target gas concentration detected by S1 exceeds a predetermined level (i.e., an alarming concentration level), a control element (not shown) opens the getter valve VG1 and switches the three-way valves V1a-V1b to redirect the sample gas stream first through the getter G1 and then through the gas sensor S2 (see FIG. 2B).

In such manner, the getter G1 is arranged and constructed to selectively adsorb the target gas from the redirected sample gas stream, thereby reducing the target gas concentration in such sample gas stream. The reduced target gas concentration after employment of the getter G1 can be readily detected by the gas sensor S2 and compared to the target gas concentration detected by gas sensor S1 before employment of the getter G1. Difference in the target gas concentrations respectively detected by S1 and S2 reflects change in the target gas concentration caused by interaction of the target gas with the getter G1. An analyzer (not shown) coupled with both the gas sensors S1-S2 and the getter G1 can selectively determine the presence of the target gas in the sample gas stream, based on such target gas concentration change.

The analyzer of the present invention may be further coupled with an alarm device (not shown), which correspondingly generates an alarm signal indicated of the presence of the target gas in the sample gas stream.

Presence of the target gas in the sample gas stream can be selectively determined by the analyzer if the detected change in the target gas concentration caused by interaction of the target gas with the getter exceeds a predetermined value, or if the target gas concentration reduces to below a predetermined threshold within a predetermined time interval after employment of the getter.

Figure 3:
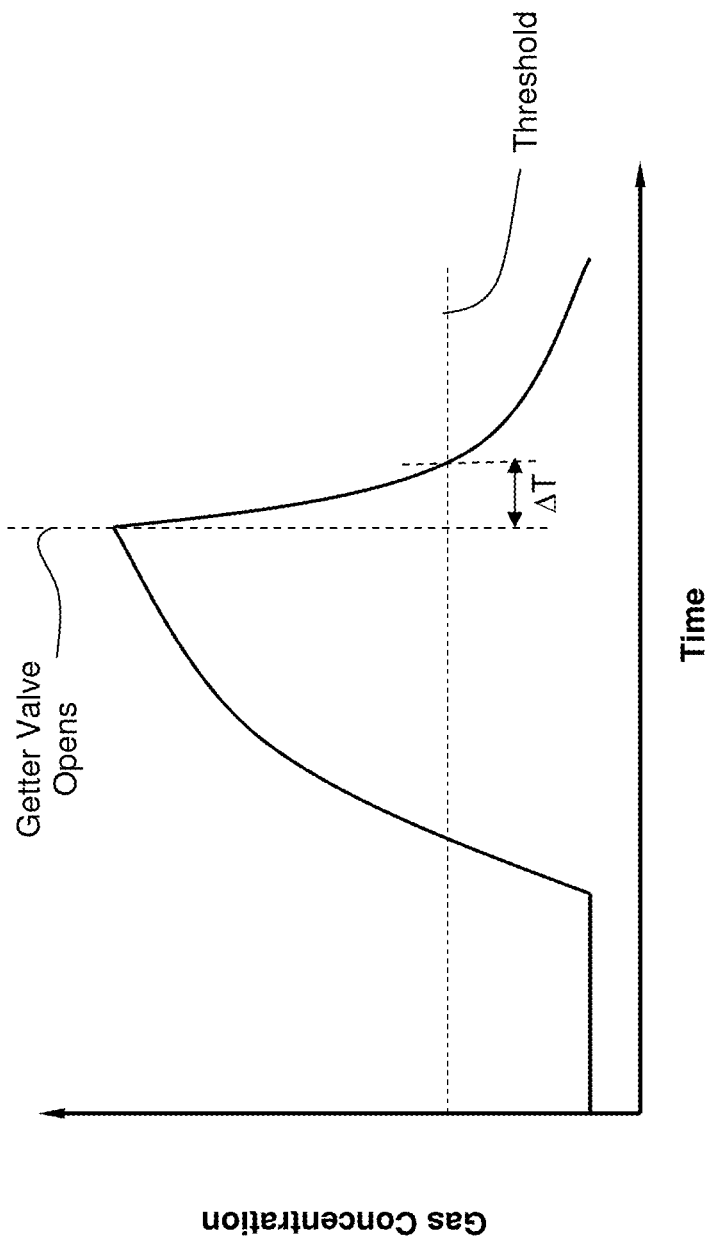
FIG. 3 illustratively shows a concentration response curve plotted for a target gas over time, which affirms the presence of such target gas in a gaseous environment being monitored.

In a preferred embodiment of the present invention, the presence of the target gas in the sample gas stream is selectively affirmed by the analyzer only if the target gas concentration reduces to below a predetermined threshold within a predetermined time interval ($\Delta T$) after employment of the getter, as shown in FIG. 3.

Such predetermined concentration threshold and predetermined time interval are specific to the target gas of interest, and also depend on the types of getter materials used for forming the getter.

Figure 4:
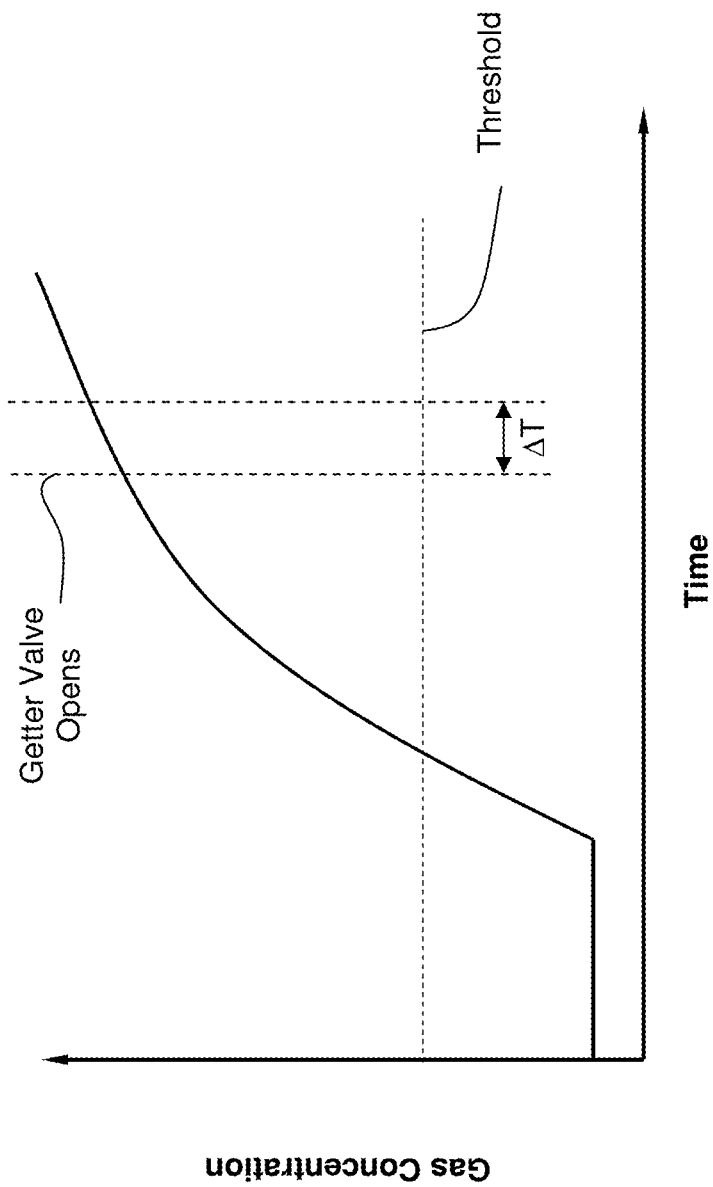
FIG. 4 illustratively shows a concentration response curve plotted for a target gas over time, which does not affirm the presence of such target gas in a gaseous environment being monitored.
Figure 5:
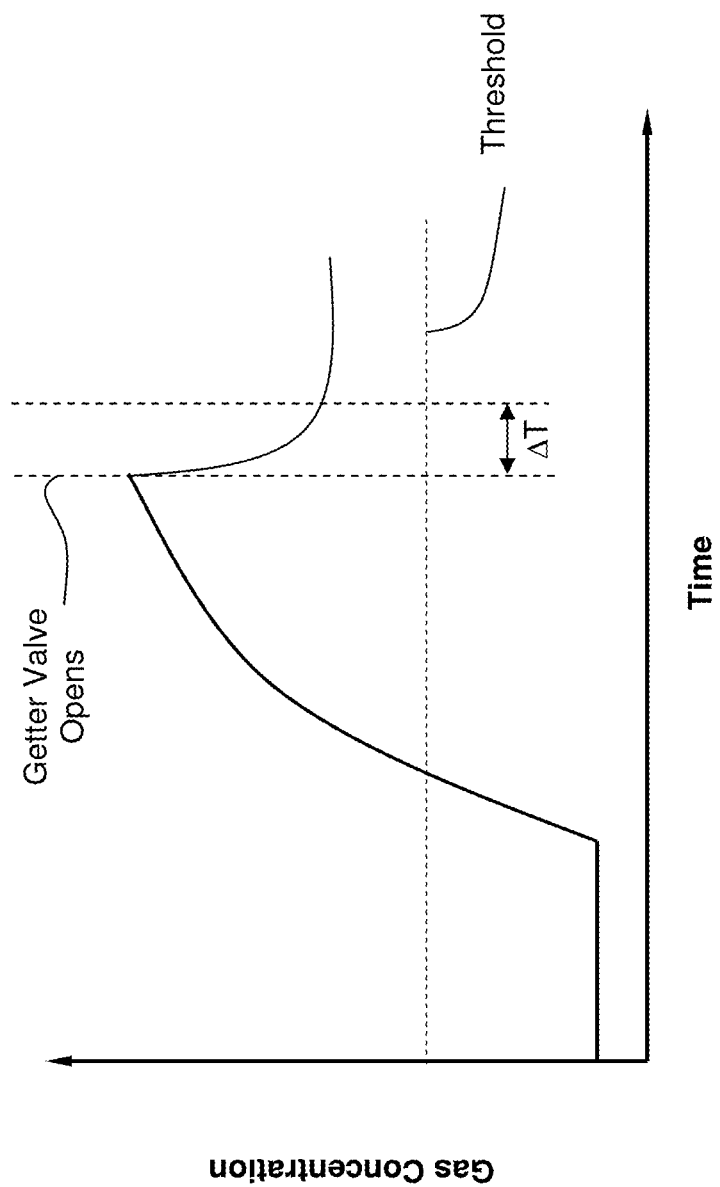
FIG. 5 illustratively shows another concentration response curve plotted for a target gas over time, which does not affirm the presence of such target gas in a gaseous environment being monitored.

FIG. 4 depicts a situation wherein the target gas concentration does not reduce at all after employment of the getter, while FIG. 5 depicts a situation wherein the target gas concentration reduces in some degree after employment of the getter, but such reduction is insufficient to set the target gas concentration to below the predetermined threshold within the predetermined time interval ($\Delta T$). In either situation, the analyzer does not affirm the presence of the target gas in the sample gas stream, and no alarm is generated.

Figure 6:
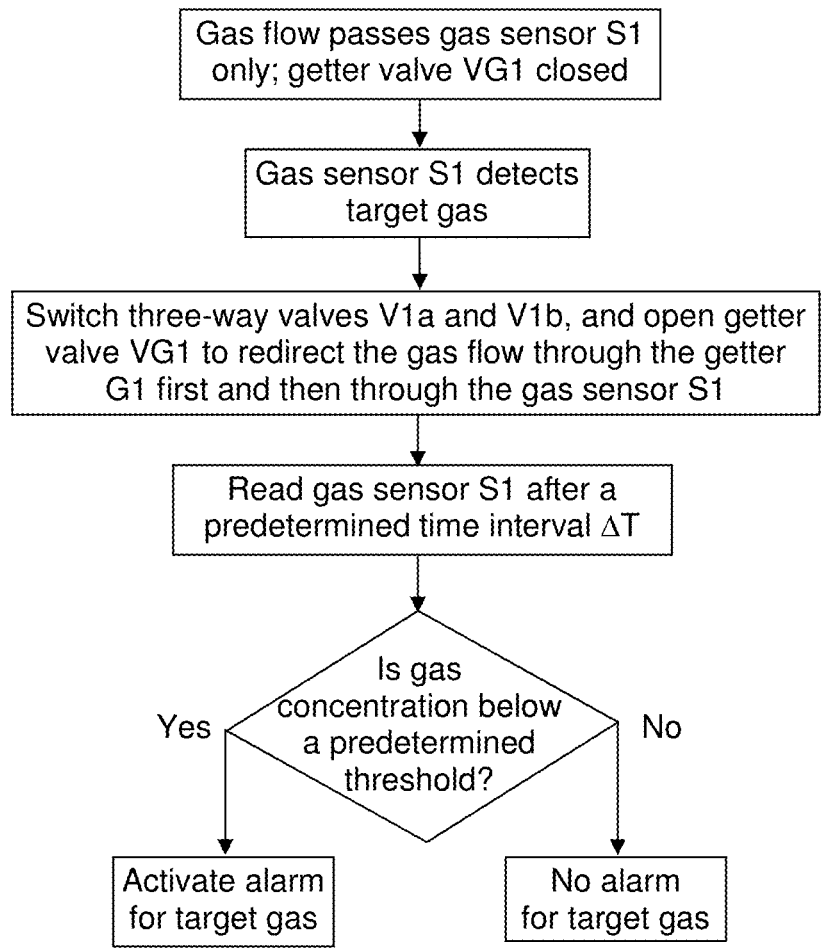
FIG. 6 is a flow chart showing a process for selectively determining the presence of a target gas by using the gas-monitoring assembly of FIGS. 1A and 1B.

FIG. 6 shows a flow chart illustrating a process for selectively determining the presence of a target gas by using the gas-monitoring assembly illustrated in FIGS. 1A and 1B, according to a specific embodiment of the present invention. Specifically, if the target gas concentration detected by the gas sensor 51 reduces to below a predetermined threshold after a predetermined time interval $\Delta T$ from the employment of the getter G1, an alarm indicative of the presence of the target gas in the sample gas stream is activated; on the other hand, if the target gas concentration detected by the gas sensor 51 does not reduce to below the predetermined threshold after the predetermined time interval $\Delta T$, no alarm is generated.

In the above-described embodiments of the present invention, the presence of the target gas in a gaseous environment is directly determined by using a getter that selectively adsorbs the target gas (i.e., a target-specific getter). Alternatively, the presence of the target gas can be indirectly inferred by using a set of getters that include a first getter that adsorbs the target gas as well as the interfering gases and additional getters that each selectively adsorbs one of the interfering gases (i.e., interference-specific getter). Such first getter and the additional getters are sequentially employed when the gas sensor detects a high concentration of the target gas. Such first getter is associated with a first predetermined time interval and a predetermined concentration threshold, while each of such additional getters is associated with an additional predetermined time interval and an additional predetermined concentration threshold. The analyzer affirms the presence of the target gas in the gaseous environment, and an alarm is generated, only if (1) the detected gas concentration is found to reduce below the first predetermined concentration threshold within the first predetermined time interval after employment of the first getter, and (2) the detected gas concentration is found to remain equal to or above the respective additional predetermined concentration threshold within the respective additional predetermined time interval after employment of each interference-specific getter. In all other situations, the analyzer does not affirm the presence of the target gas, and no alarm is generated. Specific examples for indirectly inferring the presence of a target gas in a gaseous environment are described in detail in the ensuring paragraphs.

Figure 7:
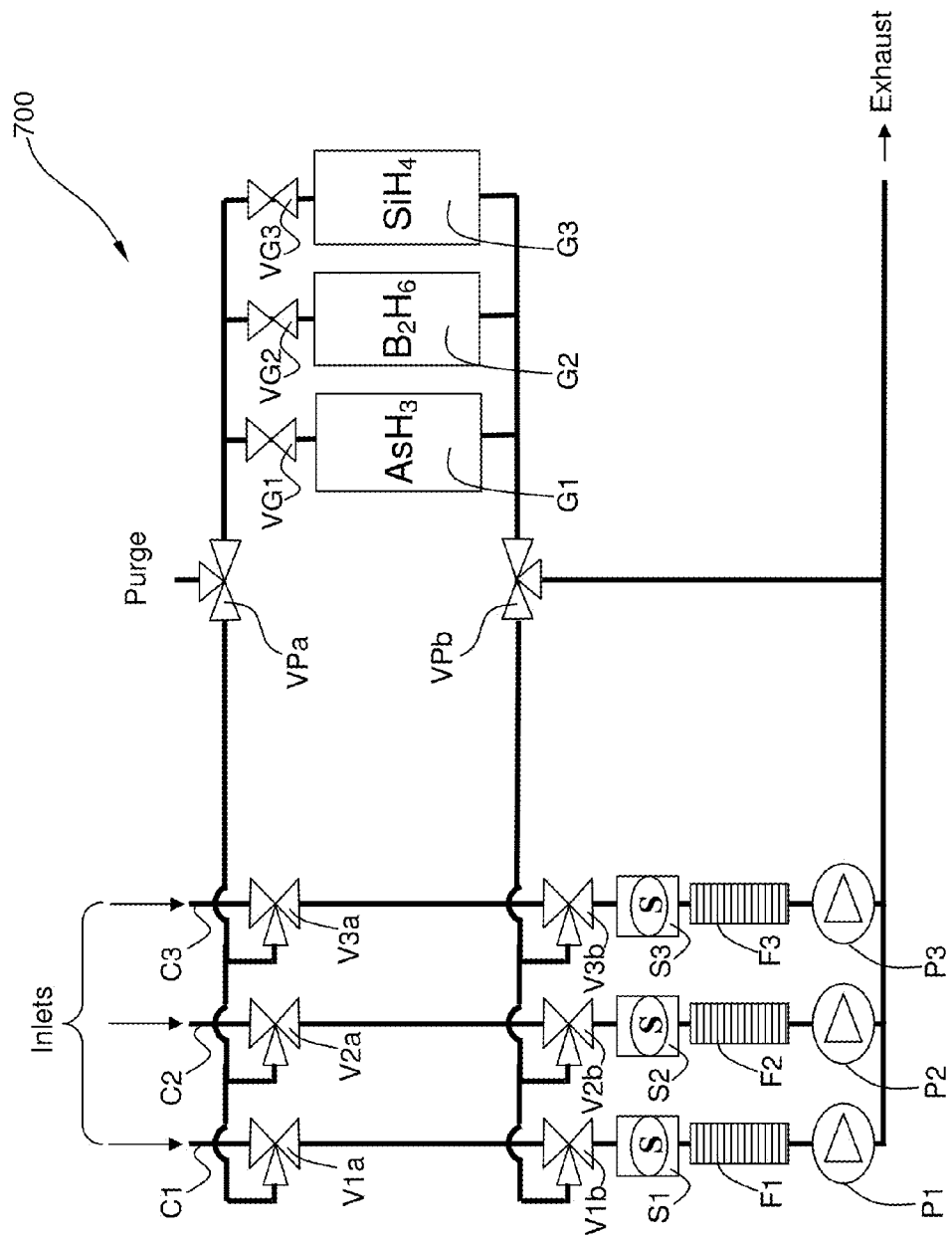
FIG. 7 shows the schematic view of a gas-monitoring assembly that comprises three gas sensors and three getters for selectively determining the presence of three different hydride gases, $AsH_3$, $B_2H_6$, and $SiH_4$, according to one embodiment of the present invention.

FIG. 7 illustrative shows a multi-channel gas-monitoring assembly 700, which comprises three different gas-monitoring channels C1, C2, and C3, for respectively monitoring and determining the presence of three different hydride gases, $AsH_3$, $B_2H_6$, and $SiH_4$ in a sample gas stream.

Each gas-monitoring channel comprises two three-way valves (V1$a$, V1$b$, V2$a$, V2$b$, V3$a$, and V3$b$) and a gas sensor (S1 for sensing $AsH_3$ gas, S2 for sensing $B_2H_6$ gas, and S3 for sensing $SiH_4$ gas).

The gas sensors S1-S3 are preferably, but not necessarily electrochemical gas sensors that each comprises an electrolyte in contact with a measuring electrode, a reference electrode, and a counter electrode. Preferably, the $AsH_3$ gas sensor S1 comprises a measuring electrode containing a catalyst formed of noble metal or noble metal alloy, including but not limited to gold, silver, platinum, and alloys thereof. The $B_2H_6$ gas sensor S2 preferably comprises a measuring electrode containing a catalyst formed of noble metal or noble metal alloy, including but not limited to gold, silver, platinum, and alloys thereof. The $SiH_4$ gas sensor S3 preferably comprises a measuring electrode containing a catalyst formed of noble metal or noble metal alloy, including but not limited to gold, silver, platinum, and alloys thereof.

Each gas-monitoring channel is further coupled with a gas analysis circuitry that comprises one or more getters selected from the group consisting of an $AsH_3$ getter G1, a $B_2H_6$ getter G2, and a $SiH_4$ getter G3 with their respective getter valves VG1-VG3.

For example, the $AsH_3$ getter may comprise $HgBr_2$ material, which selectively adsorbs $AsH_3$ gas. Such $HgBr_2$ material is preferably supported on a fibrous substrate comprising high sodium glass wool. The $B_2H_6$ getter may comprise gamma $Al_2O_3$, which selectively adsorbs $B_2H_6$ gas. The $SiH_4$ getter may comprise $AgNO_3$ and $Al(NO_3)_3$ materials, which adsorbs $SiH_4$ as well as $AsH_3$ and $B_2H_6$ gases. Such $AgNO_3$ and $Al(NO_3)_3$ materials are preferably supported on a substrate comprising gamma $Al_2O_3$. Such getter materials may be disposed in a tubular housing made of polypropylene, through which a sample gas stream may be passed for selective absorption of the respective target gas.

The multi-channel gas-monitoring assembly 700 as shown in FIG. 7 may operate in two alternative states, i.e., a gas-monitoring state in which the gas sensors S1-S3 are employed while the getters G1-G3 are not, and a gas-analyzing state in which one of the gas analysis circuitries that comprises one or more getters G1-G3 becomes activated upon detection of high concentration of a target gas in the sample gas stream by one of the gas sensors S1-S3. Such analytical circuitries and the gas sensors S1-S3 are connected with an analyzer (not shown) with stored logical operations or gas analysis protocols for further analysis of the sample gas stream and selective determination of the presence of the respective target gas in the sample gas stream.

Further, two three-way valves VPa and VPb are preferably provided for passing a purge gas through the getters G1-G3 after each analysis cycle.

Figure 8:
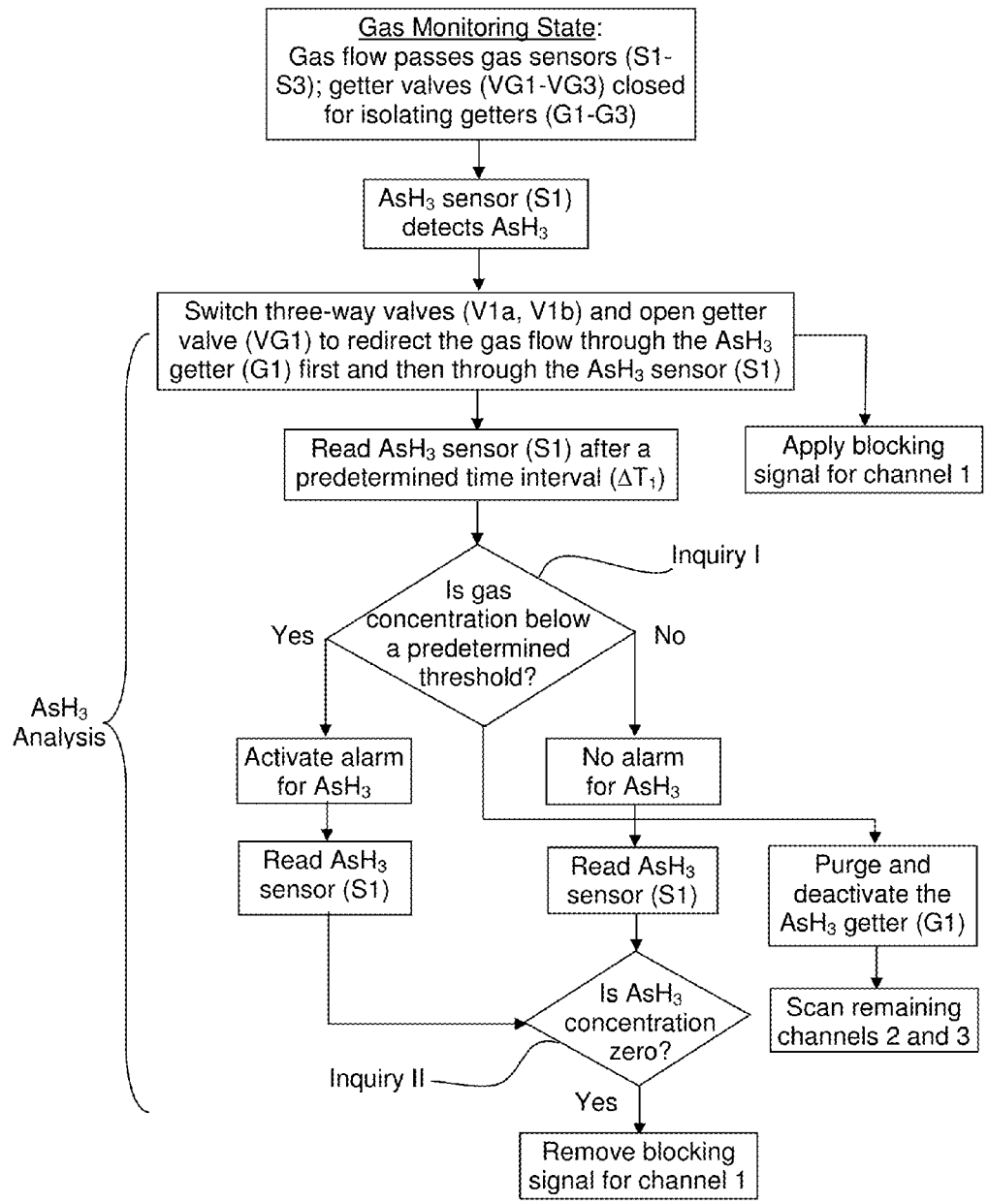
FIG. 8 is a flow chart showing a process for selectively determining the presence of $AsH_3$ gas by using the gas-monitoring assembly of FIG. 7.

FIG. 8 shows a flow chart depicting a process for $AsH_3$ analysis by using the gas-monitoring assembly 700 depicted in FIG. 7. Specifically, such process initiates from a gas-monitoring state, in which the three-way valves V1$a$, V1$b$, V2$a$, V2$b$, V3$a$, and V3$b$ of the gas-monitoring channels C1-C3 are arranged and constructed to allow the sample gas stream concurrently passing through the gas sensors S1-S3, while the getter valves VG1-VG3 are closed and the getters G1-G3 are isolated from the sample gas stream. When $AsH_3$ concentration in the sample gas stream is detected by the $AsH_3$ sensor S1 of the $AsH_3$-monitoring channel C1 as exceeding a predetermined level (i.e., an alarming concentration), a control element (not shown) opens the getter valve VG1 and switches the three-way valves V1a and V1b to redirect the sample gas stream first through the $AsH_3$ getter G1 and then through the $AsH_3$ sensor S1, In such manner, the $AsH_3$ analysis circuitry comprising the $AsH_3$ getter G1 is activated, and the $AsH_3$ analysis begins.

Upon activation of the $AsH_3$ analysis circuitry, a blocking signal is preferably generated to indicate that the $AsH_3$-monitoring channel C1 has switched from the gas-monitoring state to the gas-analyzing state.

After a predetermined time interval $\Delta T_1$ (which is specific to $AsH_3$ and the $AsH_3$ getter used) from the employment of the $AsH_3$ getter G1, the $AsH_3$ sensor S1 is read to determine whether or not the $AsH_3$ gas concentration has reduced to below a predetermined threshold that is specific to $AsH_3$, which can be referred to herein as inquiry I.

If the $AsH_3$ sensor S1 provides a positive return (i.e., yes) to inquiry I, it means that the sample gas stream comprises primarily $AsH_3$ gas with little or no interfering gases, and an alarm is generated indicating the presence of $AsH_3$ in the sample gas stream.

If the $AsH_3$ sensor S1 provides a negative return (i.e., no) to inquiry I, it means that the sample gas stream comprises significant amount of interfering gases that cannot be removed by the $AsH_3$ getter G1, and no alarm is generated for $AsH_3$ gas.

Subsequently, the three-way valves V1a and V1b are switched back to their original settings to direct the sample gas flow through the $AsH_3$ sensor S1 separate from the $AsH_3$ getter G1, while the purge valves VPa and VPb are switched to pass a purge gas through the $AsH_3$ getter G1. After purging, the getter valve VG1 closes and thereby isolates the $AsH_3$ getter G1 from the rest of the system, and system continues the gas-analysis process by scanning other channels C2 and C3.

Further, the $AsH_3$ gas sensor S1 is read again to determine whether the detected gas concentration has reduced to zero or not, as stated in inquiry II: if yes, the blocking signal for the $AsH_3$-monitoring channel C1 can be removed, and such channel may return to the gas-monitoring state for subsequent gas-monitoring; if no, the system waits until the gas concentration reduces to zero and then removes the blocking signal.

Figure 9:
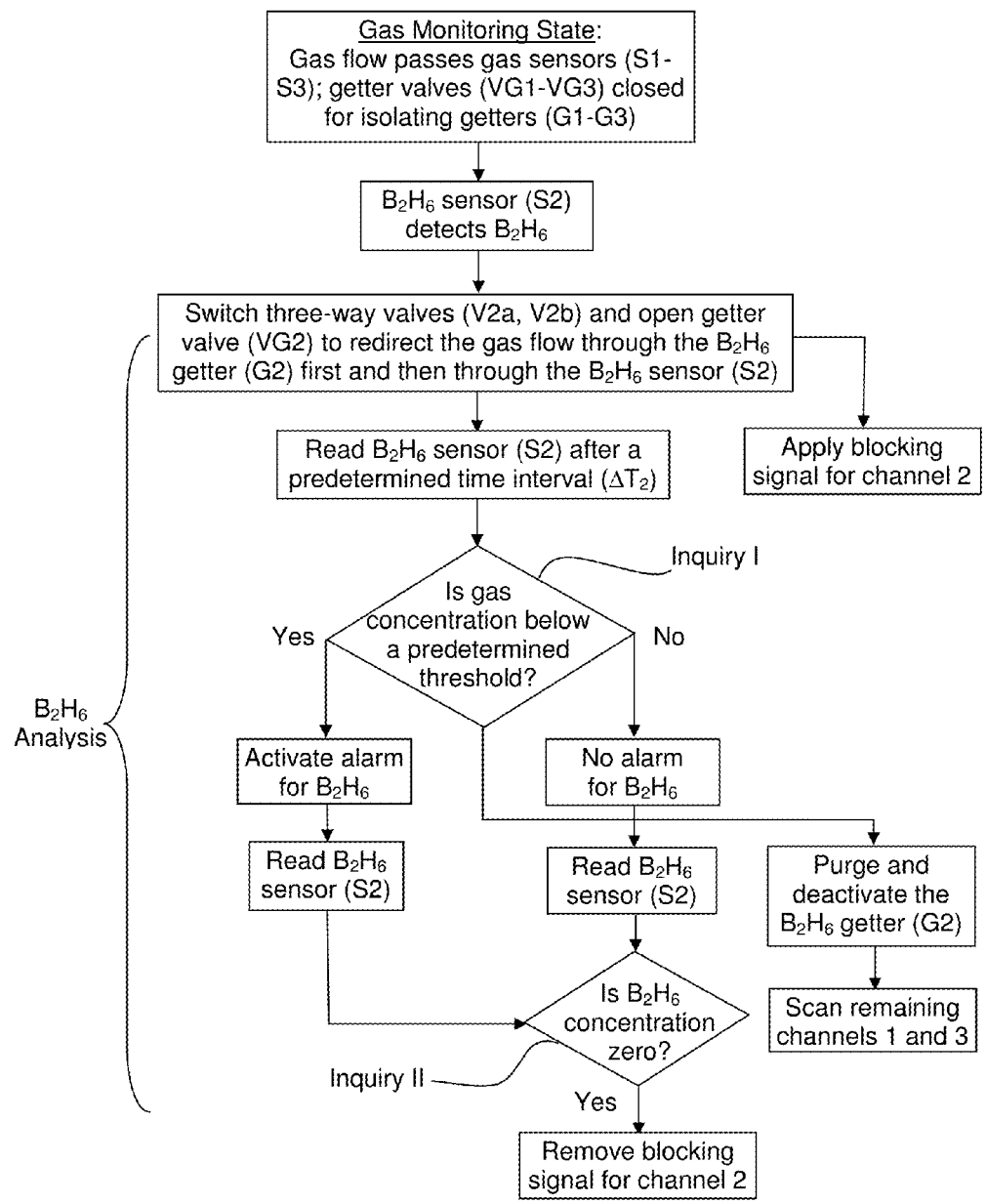
FIG. 9 is a flow chart showing a process for selectively determining the presence of $B_2H_6$ gas by using the gas-monitoring assembly of FIG. 7.

FIG. 9 shows a flow chart depicting a process for $B_2H_6$ analysis by using the gas-monitoring assembly 700 depicted in FIG. 7. Specifically, such process initiates from the same gas-monitoring state as the $AsH_3$ analysis, in which the sample gas stream concurrently passing through the gas sensors S1-S3 of the gas-monitoring channels C1-C3, while the getters G1-G3 are isolated from the sample gas stream. When $B_2H_6$ concentration in the sample gas stream is detected by the $B_2H_6$ sensor S2 of the $B_2H_6$-monitoring channel C2 as exceeding a predetermined level (i.e., an alarming concentration), a control element (not shown) opens the getter valve VG2 and switches the three-way valves V2a and V2b to redirect the sample gas stream first through the $B_2H_6$ getter G2 and then through the $B_2H_6$ sensor S2. In such manner, the $B_2H_6$ analysis circuitry comprising the $B_2H_6$ getter G2 is activated, and the $B_2H_6$ analysis begins.

Upon activation of the $B_2H_6$ analysis circuitry, a blocking signal is preferably generated to indicate that the $B_2H_6$-monitoring channel C2 has switched from the gas-monitoring state to the gas-analyzing state.

After a predetermined time interval $\Delta T_2$ (which is specific to $B_2H_6$ and the $B_2H_6$ getter used) from the employment of the $B_2H_6$ getter G2, the $B_2H_6$ sensor S2 is read to determine whether or not the $B_2H_6$ gas concentration has reduced to below a predetermined threshold that is specific to $B_2H_6$, which can be referred to herein as inquiry I.

If the $B_2H_6$ sensor S2 provides a positive return (i.e., yes) to inquiry I, it means that the sample gas stream comprises primarily $B_2H_6$ gas with little or no interfering gases, and an alarm is generated indicating the presence of $B_2H_6$ in the sample gas stream.

If the $B_2H_6$ sensor S2 provides a negative return (i.e., no) to inquiry I, it means that the sample gas stream comprises significant amount of interfering gases that cannot be removed by the $B_2H_6$ getter G2, and no alarm is generated for $B_2H_6$ gas.

Subsequently, the three-way valves V2a and V2b are switched back to their original settings to direct the sample gas flow through the $B_2H_6$ sensor S2 separate from the $B_2H_6$ getter G2, while the purge valves VPa and VPb are switched to pass a purge gas through the $B_2H_6$ getter G2. After purging, the getter valve VG2 $B_2H_6$ closes and thereby isolates the $B_2H_6$ getter G2 from the rest of the system, and system continues the gas-analysis process by scanning other channels C1 and C3.

Further, the $B_2H_6$ gas sensor S2 is read again to determine whether the detected gas concentration has reduced to zero or not, as stated in inquiry II: if yes, the blocking signal for the $B_2H_6$-monitoring channel C2 can be removed, and such channel may return to the gas-monitoring state for subsequent gas-monitoring; if no, the system waits until the gas concentration reduces to zero and then removes the blocking signal.

For $SiH_4$ analysis, if the $SiH_4$ getter G3 selectively adsorbs the $SiH_4$ gas but not the other hydrides such as $AsH_3$ and $B_2H_6$, the analytical process steps for $SiH_4$ is then substantially similar to those described for $AsH_3$ or $B_2H_6$ analysis, in which the presence of $SiH_4$ is directly determined based on the selective absorption of $SiH_4$ by the $SiH_4$ getter G3.

Figure 10A:
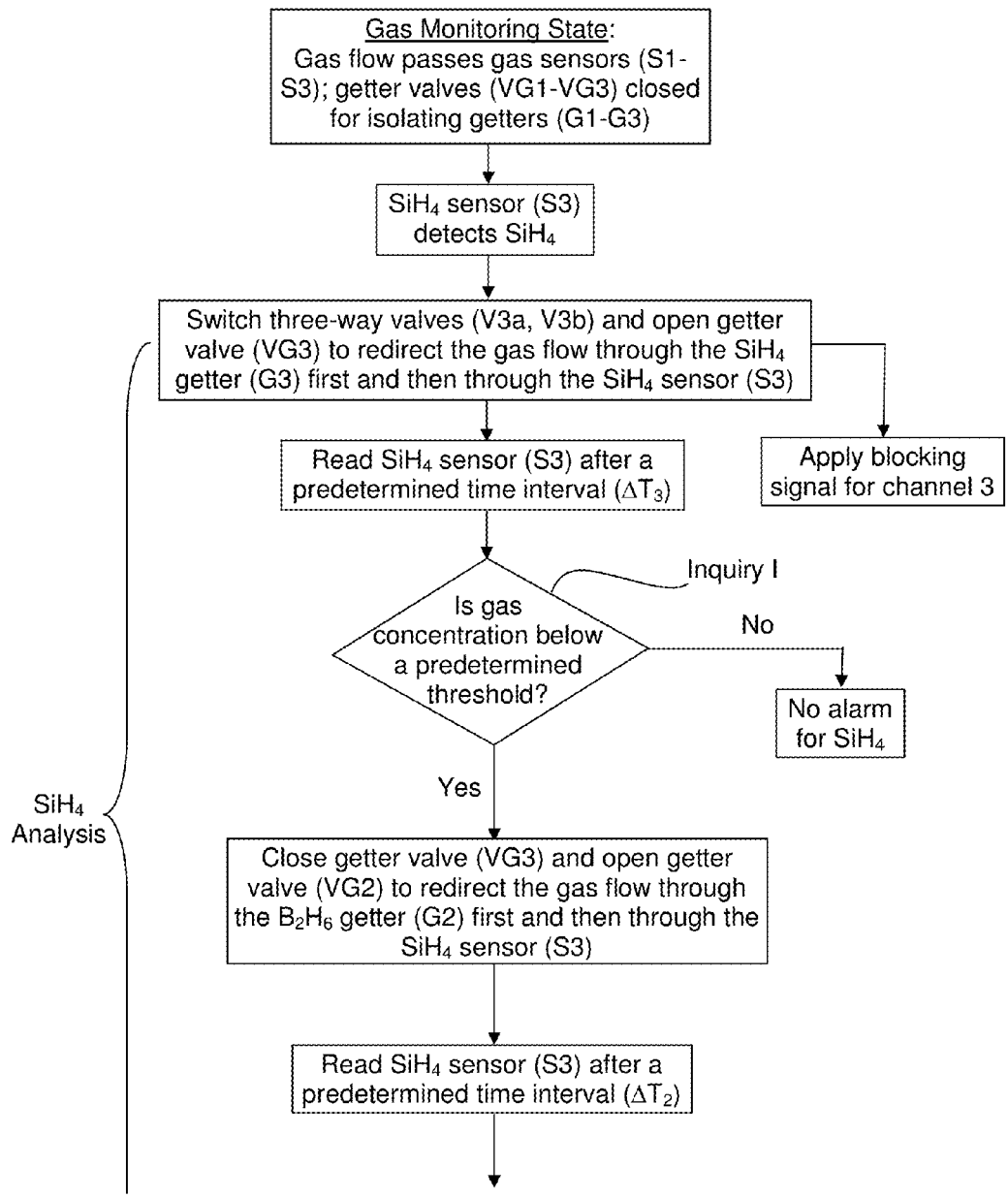
FIGS. 10A-10B shows a flow chart depicting a process for selectively determining the presence of $SiH_4$ gas by using the gas-monitoring assembly of FIG. 7.
Figure 10B:
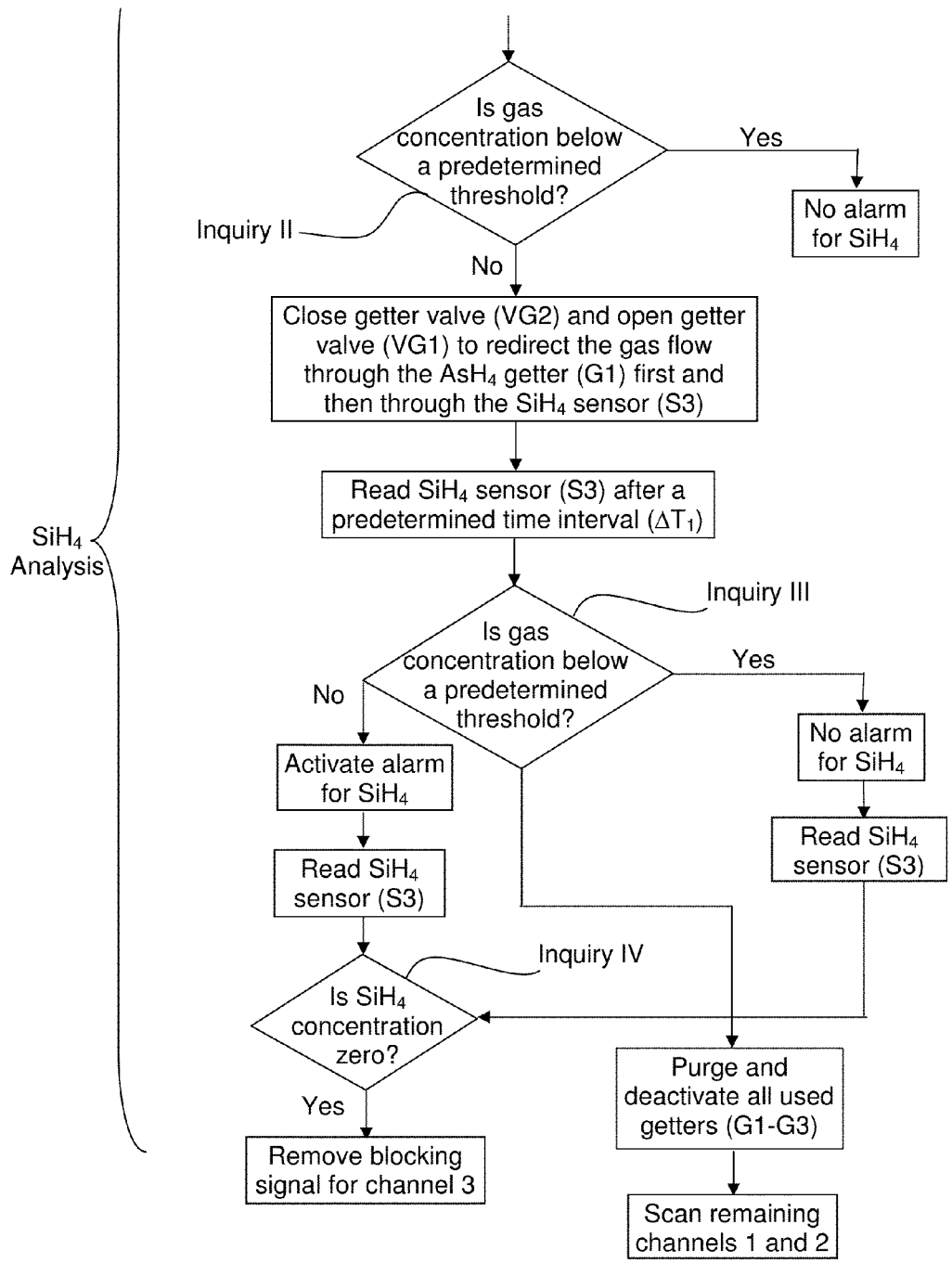

However, if the $SiH_4$ getter G3 adsorbs not only $SiH_4$ but also $AsH_3$ and $B_2H_6$ gases, a $SiH_4$ analytical circuitry comprising the $SiH_4$ getter G3, the $B_2H_6$ getter G2, and the $AsH_3$ getter G1 can be provided to indirectly infer the presence of $SiH_4$ in a sample gas stream that potentially contains $SiH_4$, $AsH_3$, or $B_2H_6$, based on logical exclusion as shown in FIGS. 10A and 10B.

Specifically, such $SiH_4$ analytical process initiates from the same gas-monitoring state as the $AsH_3$ and $B_2H_6$ analysis, in which a sample gas stream is concurrently passing through the gas sensors S1-S3 of the gas-monitoring channels C1-C3, while the getters G1-G3 are isolated from the sample gas stream.

When $SiH_4$ concentration in the sample gas stream is detected by the $SiH_4$ sensor S3 of the $SiH_4$-monitoring channel C3 as exceeding a predetermined level (i.e., an alarming concentration), a control element (not shown) opens the getter valve VG3 and switches the three-way valves V3a and V3b to redirect the sample gas stream first through the $SiH_4$ getter G3 and then through the $SiH_4$ sensor S3. In such manner, the $SiH_4$ analysis begins by sequentially employing the $SiH_4$ getter G3, the $B_2H_6$ getter G2, the $AsH_3$ getter G1 contained in the $SiH_4$ analysis circuitry to interact with the sample gas stream.

It is important to note that although the sequential employment of the getters G1-G3 preferably proceeds in a predetermined order, such as G3→G2→G1 or G1→G2→G3, it may proceed in any random order without limitation, and the analytical logic can be readily modified by a person ordinarily skilled in the art to adapt to any specific order.

Upon activation of the $SiH_4$ analysis circuitry, a blocking signal is preferably generated to indicate that the $SiH_4$-monitoring channel C3 has switched from the gas-monitoring state to the gas-analyzing state.

After a predetermined time interval $\Delta T_3$ (which is specific to $SiH_4$ and the $SiH_4$ getter used) from the employment of the $SiH_4$ getter G3, the $SiH_4$ sensor S3 is read to determine whether or not the $SiH_4$ gas concentration has reduced to below a predetermined threshold that is specific to $SiH_4$, which can be referred to herein as inquiry I.

If the $SiH_4$ sensor S3 provides a negative return (i.e., no) to inquiry I, it means that the sample gas stream contains significant amount of interfering gases that are not $SiH_4$, $B_2H_6$, or $AsH_3$ and cannot be removed by the $SiH_4$ getter G3, and no alarm is generated for $SiH_4$ gas.

If the $SiH_4$ sensor S3 provides a positive return (i.e., yes) to inquiry I, it means that the sample gas stream contains $SiH_4$, $B_2H_6$, or $AsH_3$ gas with little or no other interfering gases, and the system proceeds further to determine whether the sample gas stream comprises primarily $B_2H_6$, by closing the getter valve VG3 and opening the getter valve VG2 to redirect the sample gas stream first through the $B_2H_6$ getter G2 and then the $SiH_4$ sensor S3. In such manner, the $B_2H_6$ getter G2 contained in the $SiH_4$ analytical circuitry is employed.

After a predetermined time interval $\Delta T_2$ (which is specific to $B_2H_6$ and the $B_2H_6$ getter used) from the employment of the $B_2H_6$ getter G2, the $SiH_4$ sensor S3 is read to determine whether or not the detected gas concentration has reduced to below a predetermined threshold that is specific to $B_2H_6$, which can be referred to herein as inquiry II.

If the $SiH_4$ sensor S3 provides a positive return (i.e., yes) to inquiry II, it means that the sample gas stream comprises primarily $B_2H_6$ gas with little or no other hydride gases, and therefore no alarm is generated for $SiH_4$ gas.

If the $SiH_4$ sensor S3 provides a negative return (i.e., no) to inquiry II, it means that the sample gas stream comprises significant amount of hydride gas(es) that is not $B_2H_6$ and cannot be removed by the $B_2H_6$ getter G2, and the system proceeds further to determine whether the sample gas stream comprises primarily $AsH_3$, by closing the getter valve VG2 and opening the getter valve VG1 to redirect the sample gas stream first through the $AsH_3$ getter G1 and then the $SiH_4$ sensor S3. In such manner, the $AsH_3$ getter G1 contained in the $SiH_4$ analytical circuitry is employed.

After a predetermined time interval $\Delta T_1$ (which is specific to $AsH_3$ and the $AsH_3$ getter used) from the employment of the $AsH_3$ getter G1, the $SiH_4$ sensor S3 is read to determine whether or not the detected gas concentration has reduced to below a predetermined threshold that is specific to $AsH_3$, which can be referred to herein as inquiry III.

If the $SiH_4$ sensor S3 provides a positive return (i.e., yes) to inquiry III, it means that the sample gas stream comprises primarily $AsH_3$ gas with little or no other hydride gases, and therefore no alarm is generated for $SiH_4$ gas.

If the $SiH_4$ sensor S3 provides a negative return (i.e., no) to inquiry III, it means that the sample gas stream comprises significant amount of hydride gas(es) that is not $AsH_3$ and cannot be removed by the $AsH_3$ getter G1. At this point, it is determined that the sample gas stream likely contains $SiH_4$ gas, based on the observations that (1) the sample gas stream contains $SiH_4$, $B_2H_6$, or $AsH_3$ gas with little or no other interfering gases; (2) the sample gas stream comprises significant amount of hydride gas(es) that is not $B_2H_6$, and (3) the sample gas stream comprises significant amount of hydride gas(es) that is not $AsH_3$, as obtained from the above-described analytical steps. Consequently, an alarm can be generated to indicate the presence of $SiH_4$ gas in the sample gas stream.

Subsequently, the three-way valves V3a and V3b are switched back to their original settings to direct the sample gas flow through the $SiH_4$ sensor S3 separate from the $AsH_3$ getter G1, while the purge valves VPa and VPb and all the getter valves VG1-VG3 are opened to pass the purge gas through all the getters G1-G3 that have been used during the $SiH_4$ analysis. After purging, the getter valves VG1-VG3 are closed and thereby isolate the respective getters G1-G3 from the rest of the system, and system continues the gas-analysis process by scanning other channels C1 and C2.

Further, the $SiH_4$ gas sensor S3 is read again to determine whether the detected gas concentration has reduced to zero or not, as stated in inquiry IV: if yes, the blocking signal for the $SiH_4$-monitoring channel C3 can be removed, and such channel may return to the gas-monitoring state for subsequent gas-monitoring; if no, the system waits until the gas concentration reduces to zero and then removes the blocking signal.

Although the above-description is directed primarily to detection of hydride gases such as $AsH_3$, $B_2H_6$, and $SiH_4$, etc., the present invention is also applicable to various different target gas species, including but not limited to other hydrides, halogens, mineral acids, fluorinated hydrocarbons, ammonia, etc., and their respective derivatives, and a person ordinarily skilled in the art can readily modify the configurations of the gas-sensing assemblies as described hereinabove for detection and analysis of specific target gas species, consistent with the principles of the present invention.

Figure 11:
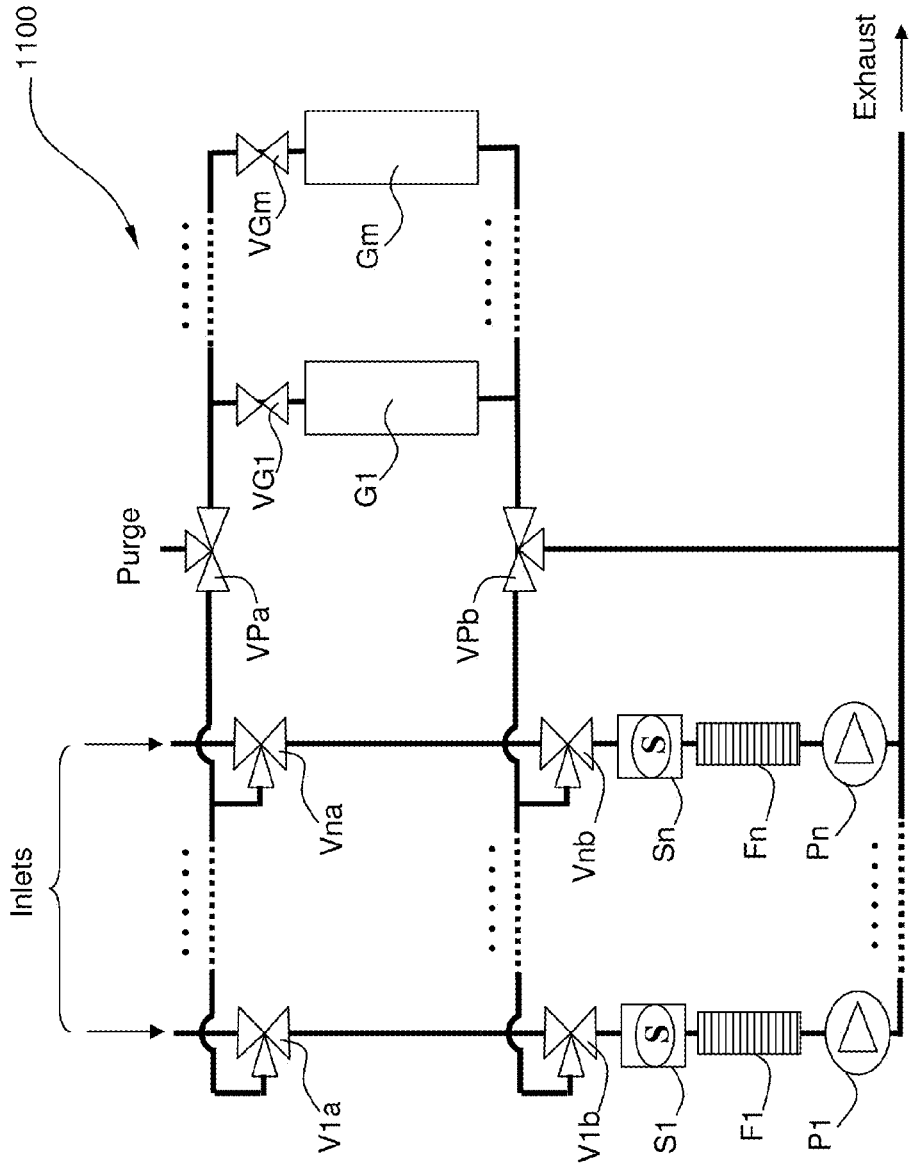
FIG. 11 shows the schematic view of a generalized gas-monitoring assembly that comprises multiple gas-monitoring elements and multiple getters for selectively determining the presence of multiple target gases, according to one embodiment of the present invention.

FIG. 11 therefore depicts a generalized multi-channel gas-monitoring assembly 1100, which comprises n different gas-monitoring channels, each of which contains valves V1a and V1b, gas sensor Si, flow meter Fi, and pump Pi (wherein i is from 1 to n), and each of which is coupled with a gas analysis circuitry that comprises one or more getters selected from G1-Gm, while each getter Gj can be exposed to and isolated from the rest of the assembly 1100 by a getter valve VGj (wherein j is from 1 to m). The purge valves VPa and VPb function to purge the getters contained the respective gas analysis circuitry after each gas analysis cycle.

Figure 12:
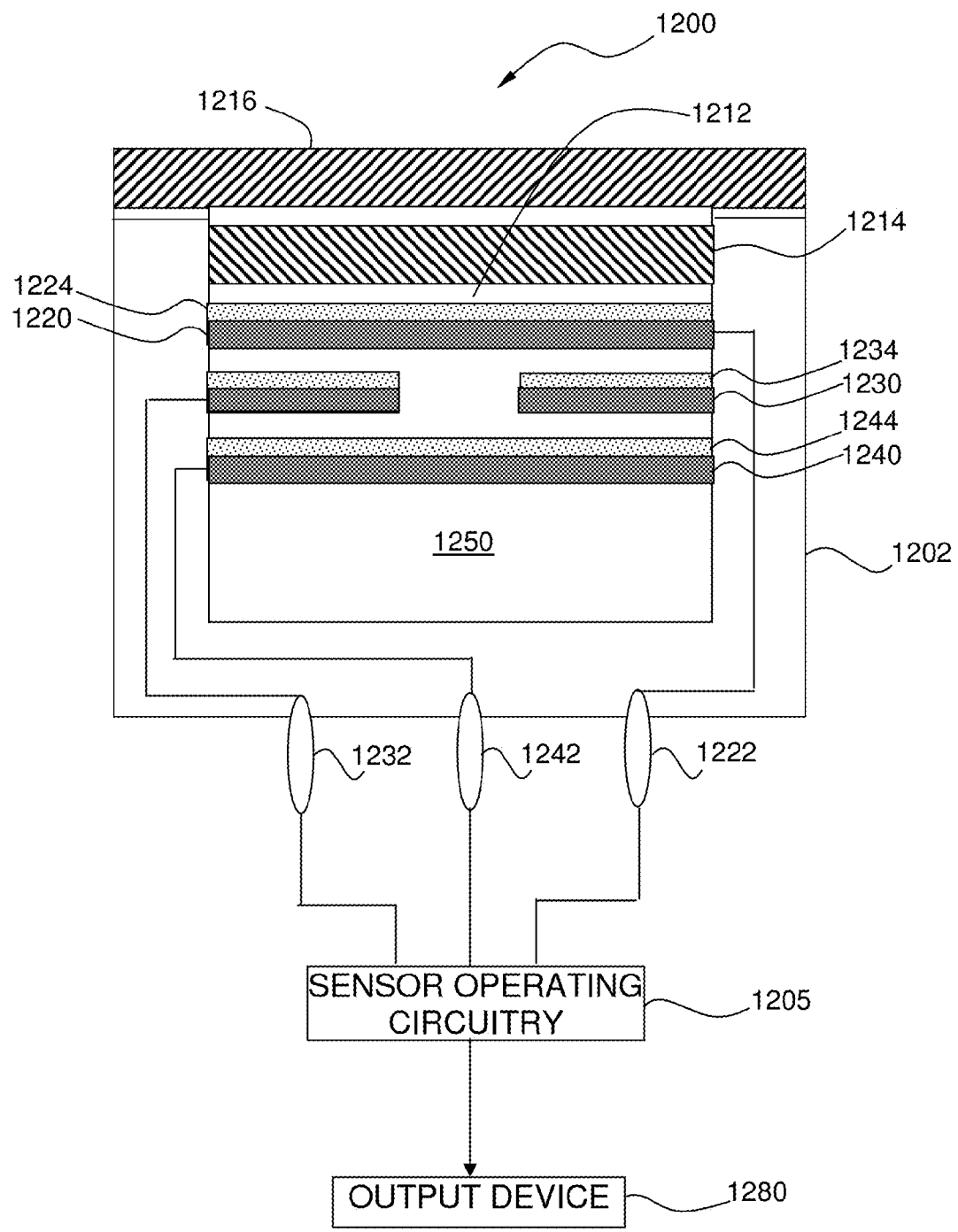
FIG. 12 shows an exemplary electrochemical gas sensor for monitoring concentration of a target gas, according to one embodiment of the present invention.
Figure 13:
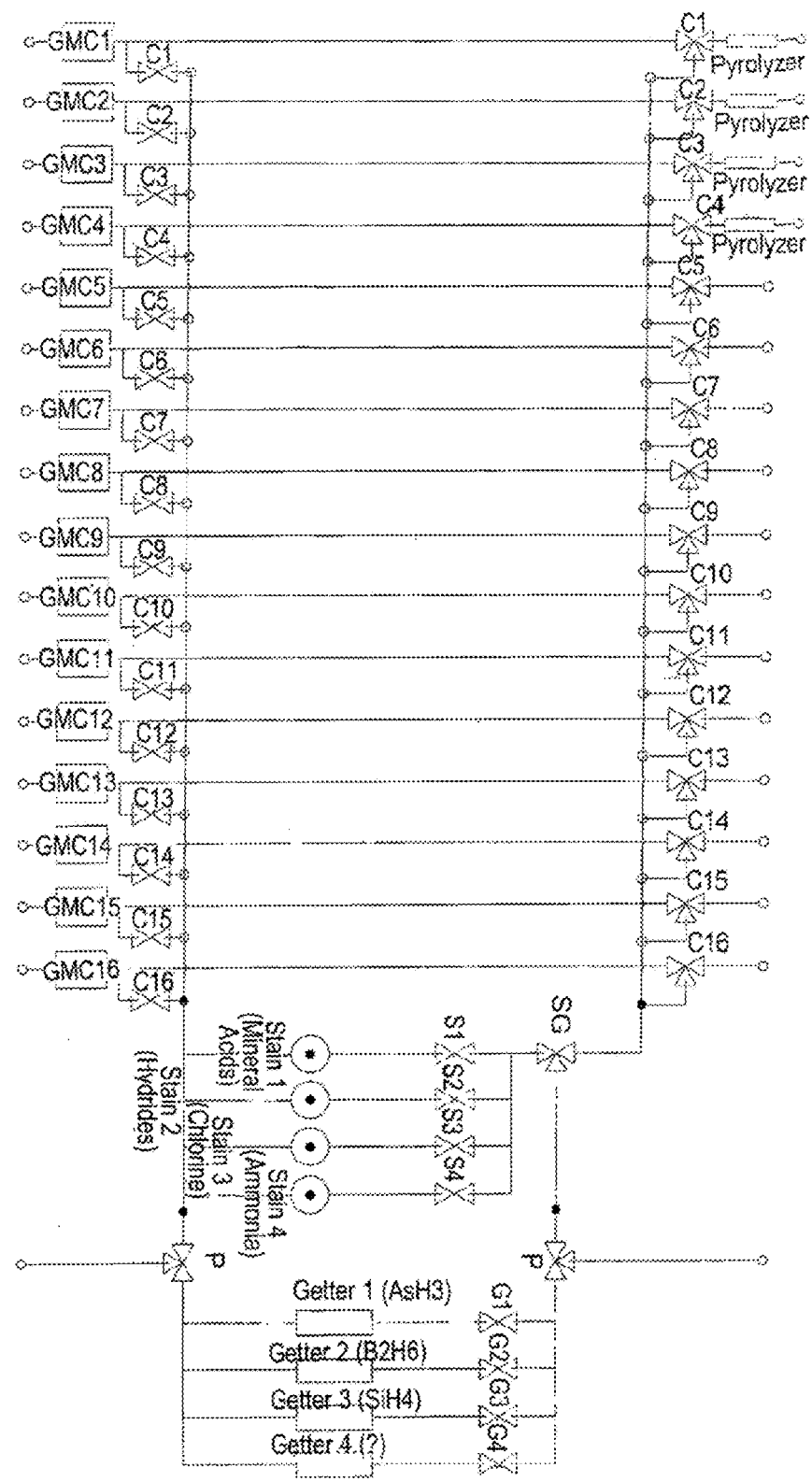
FIG. 13 shows a schematic view of a gas monitoring assembly that comprises four optical sensors for selectively determining the presence of mineral acids, hydrides, chlorine, and amino, and three getters for selectively determining the presence of three different hydride gases $AsH_3$, $B_2H_6$, $SiH_4$.

The gas sensing elements S1-Sn preferably comprises one or more electrochemical gas sensors as illustrated in FIG. 12.

Specifically, the electrochemical gas sensor 1200 of FIG. 12 comprises a measuring electrode 1220 comprising a catalyst to sense one or more suitable target gases. Such measuring electrode 1220 is preferably positioned inside a sensor cell 1202 and conductively coupled to a sensor operating circuitry 1205. Sensor operating circuitry 1205 for one embodiment may also be coupled to or in wireless communication with an output device 1280. Output device 1280 may be local to or remote from sensor operating circuitry 1205 and may or may not be a component of sensor 1200.

Sensor cell 1202 further comprises a reference electrode 1230, a counter electrode 1240, an electrolyte 1250, and electrical contacts 1222, 1232, and 1242. Although described as having three electrodes, sensor cell 1202 for another embodiment may have only two electrodes or may have more than three electrodes. Sensor cell 1202 for another embodiment may not have reference electrode 1230, for example.

The sensor cell 1202 defines an electrolyte reservoir of any suitable size and shape to hold electrolyte 1250 and is configured to help support measuring electrode 1220, reference electrode 1230, and counter electrode 1240 such that at least a portion of each of measuring electrode 1220, reference electrode 1230, and counter electrode 1240 are coupled to electrolyte 1250. The measuring electrode 1220 may be supported in any suitable position in the electrolyte reservoir such that at least a portion of measuring electrode 1220 is immersed in electrolyte 1250. The reference electrode 1230 and counter electrode 1240 may also be supported in any suitable position in the electrolyte reservoir such that both reference electrode 1230 and counter electrode 1240 are immersed in electrolyte 1250.

Measuring electrode 1220, reference electrode 1230, and counter electrode 1240 for one embodiment may each have any suitable size and shape for positioning in the electrolyte reservoir. Where the electrolyte reservoir is shaped as a hollowed cylinder, for example, measuring electrode 1220 for one embodiment may be disc-shaped and reference electrode 1230 and counter electrode 1240 for one embodiment may be ring-shaped or disc-shaped.

The sensor cell 1202 in one embodiment comprises an opening 1212 of any suitable size and shape through which a target gas may pass from an external environment to contact measuring electrode 1220. For one embodiment, a membrane 1224 is provided in any suitable position relative to opening 1212 and to measuring electrode 1220 to allow a target gas to diffuse through membrane 1224 to measuring electrode 1220 and to help prevent electrolyte 1250 from passing through membrane 1224 and out of the electrolyte reservoir. Membrane 1224 for one embodiment, as illustrated in FIG. 12, may be coupled to measuring electrode 1220. Membrane 1224 may be formed from any suitable material, such as polytetrafluoroethylene (PTFE) for example.

An optional chemical filter 1214 may be provided in any suitable position relative to opening 1212 to help prevent one or more poisons that may damage measuring electrode 1220 and/or one or more potentially interfering non-target gases that may otherwise be sensed by measuring electrode 1220 as target particles from reaching measuring electrode 1220. An optional dust filter 1216 may also be provided in any suitable position relative to opening 1212 to help prevent dust, dirt, mites, etc. from interfering with sensor cell 1202.

Reference electrode 1230 may be formed in any suitable manner from any suitable material. Reference electrode 1230 for one embodiment may be formed similarly as measuring electrode 1220. Reference electrode 1230 for one embodiment may be formed by mixing a suitable powder or powder mixture for reference electrode 1230 with a powder or emulsion of a suitable binder material, such as polytetrafluoroethylene (PTFE) for example, to produce an emulsion that may be spread onto a suitable porous substrate 1234 for mechanical strength. Substrate 1234 for one embodiment may also serve as a diffusion barrier. Substrate 1234 for one embodiment may then be subjected to a suitable heat treatment to help bond the emulsion to the substrate and remove solvents. Substrate 1234 may be formed from any suitable material, such as polytetrafluoroethylene (PTFE) for example.

Counter electrode 1240 may be formed in any suitable manner from any suitable material that may depend, for example, on the reaction to be catalyzed by counter electrode 1240. Further, a suitable membrane 1244 may be provided in any suitable position relative to the opening 1212 and to counter electrode 1240 to allow gases (such as oxygen gas or moisture) necessary for the electrochemical reactions to diffuse therethrough to counter electrode 1240 and to help prevent electrolyte 1250 from passing out of the electrolyte reservoir.

Counter electrode 1240 for one embodiment may be formed by mixing a suitable powder or powder mixture for counter electrode with a powder or emulsion of a suitable binder material, such as polytetrafluoroethylene (PTFE) for example, to produce an emulsion that may be spread onto a suitable porous substrate 1244 for mechanical strength. Substrate 1244 for one embodiment may also serve as a diffusion barrier. Substrate 1244 for one embodiment may then be subjected to a suitable heat treatment to help bond the emulsion to the substrate and remove solvents. Substrate 1244 may be formed from any suitable material, such as polytetrafluoroethylene (PTFE) for example.

The measuring electrode 1220, reference electrode 1230, and counter electrode 1240 may be coupled with the electrolyte 1250 in any other suitable manner. For example, the measuring electrode 1220, reference electrode 1230, and/or counter electrode 1240 external to an electrolyte reservoir may be coupled with an electrolyte through wetting filters or porous walls that help to define the reservoir.

Electrical contacts 1222, 1232, and 1242 are conductively coupled to measuring electrode 1220, reference electrode 1230, and counter electrode 1240, respectively. Electrical contacts 1222, 1232, and 1242 are to be conductively coupled to sensor operating circuitry 1205 to conductively couple measuring electrode 1220, reference electrode 1230, and counter electrode 1240, respectively, to sensor operating circuitry 1205. Electrical contacts 1222, 1232, and 1242 may be shaped as pins for insertion into corresponding socket openings of a connector for sensor operating circuitry 1205, in a specific embodiment of the present invention. Electrical contacts 1222, 1232, and 1242 for another embodiment may be shaped in any other suitable manner.

For another embodiment, sensor operating circuitry 1205 may be directly coupled to measuring electrode 1220, reference electrode 1230, and counter electrode 1240.

Sensor operating circuitry 1205 functions to operate sensor 1200 to sense one or more target gases in a gaseous environment near sensor cell 1202. Sensor operating circuitry 1205 may be conductively coupled to sensor cell 1202 either locally in or near the same environment or remotely.

In a further aspect of the invention, a multi-channel gas-monitoring assembly is provided comprising at least one colorimetric sensor element. Some chemicals will change color in chemical reaction when they are exposed to other chemicals. This concept can be used according to the invention in combination with the above gas-monitoring assembly. The principle of this technology is a color change of an indicator substance in case of a gas exposure. Thereby, a "stain" is made which can then be detected for example visually or electronically. According to a preferred embodiment of the invention, a chemically impregnated tape is used to monitor gases which may be hazardous or toxic. The change of color can be detected and analyzed by optical devices known in the art such as photocells and converted to a gas concentration. According to a preferred embodiment of the invention, at least one electrochemical gas sensor is combined with a colorimetric sensor element within a multi-channel device. In case of an alarm from the electrochemical gas sensor a by-pass will open and the gas will flow to a colorimetric sensor element. According to a more preferred embodiment of the invention said colorimetric element is a chemically impregnated tape, preferably a paper tape. A visual inspection of the paper tape makes it possible to determine whether a gas exposure has taken place. By variation of the used indicator substance, a detection of a large variety of different gases is possible. This method provides a physical evidence of a gas exposure in form of a stain on the tape.

The combination of at least one electrochemical gas sensor and at least one colorimetric element according to the invention combines the advantages of the individual technologies. The paper tape color change element provides a physical evidence of a gas leak which may be required for proper safety documentation. According to the invention, any paper tape can be used which is commercially available. Depending on which gas shall be proven, different indicator substances can be used. It is possible according to the invention to use special chemicals which change their color when brought into contact with a special gas as for example mineral acids, hydrides, chlorine, ammonia etc.

While the invention has been described herein with reference to specific aspects, features and embodiments, it will be recognized that the invention is not thus limited, but rather extends to and encompasses other variations, modifications and alternative embodiments. Accordingly, the invention is intended to be broadly interpreted and construed to encompass all such other variations, modifications, and alternative embodiments, as being within the scope and spirit of the invention as hereinafter claimed.

What is claimed is:

1. A gas-monitoring assembly comprising at least one gas sensor, a gas analysis circuitry, and a control element coupling the gas sensor to the gas analysis circuitry, wherein said gas sensor monitors concentration of a target gas in a gaseous environment, wherein the gas analysis circuitry comprises one or more getters, wherein said gas analysis circuitry is configured for activation upon detection of the target gas concentration above a predetermined level by the at least one gas sensor, for selectively determining presence of the target gas in said gaseous environment while reducing potential cross-interference caused by presence of one or more interfering gas species in said gaseous environment and wherein the control element is configured to direct flow of the monitored gas to the gas analysis circuitry upon detection of the target gas concentration by the at least one gas sensor.

2. A gas-monitoring assembly comprising:

(a) one or more gas sensors for monitoring concentration of a target gas in a gaseous environment, wherein the target gas concentration detected by said gas sensors is susceptible to influence by presence of one or more interfering gas species in said gaseous environment;

(b) one or more getters coupled with said gas sensors and configured for activation to adsorb the target gas and/or said one or more interfering gas species upon detection of the target gas concentration above a predetermined level in said gaseous environment;

(c) an analyzer coupled with said one or more gas sensors and said one or more getters for selectively determining the presence of the target gas in said gaseous environment, based on changes in the target gas concentration caused by interaction of the target gas with said one or more getters in relation to target gas concentration absent such interaction; and (d) at least one colorimetric sensor element which changes color in case of a gas exposure connected to said gaseous environment such that gas from said gaseous environment can be supplied to said at least one colorimetric sensor element upon detection of the target gas concentration above a predetermined level in said gaseous environment.

* * * * *